United States Patent [19]

Schulte et al.

[11] Patent Number: 4,681,560
[45] Date of Patent: Jul. 21, 1987

[54] SUBCUTANEOUS INFUSION RESERVOIR AND PUMP SYSTEM

[75] Inventors: Rudolf R. Schulte, Santa Barbara; Gary P. East; Alfons Heindl, both of Goleta, all of Calif.

[73] Assignee: Pudenz-Schulte Medical Research Corp., Santa Barbara, Calif.

[21] Appl. No.: 850,943

[22] Filed: Apr. 11, 1986

Related U.S. Application Data

[63] Continuation-in-part of Ser. No. 590,349, Mar. 16, 1984, Pat. No. 4,588,394.

[51] Int. Cl.⁴ .............................................. A61M 5/00
[52] U.S. Cl. ............................................ 604/9; 604/8
[58] Field of Search ...................................... 604/8–10, 604/175, 181, 183, 185, 186, 891, 247, 246

[56] References Cited

U.S. PATENT DOCUMENTS

| | | |
|---|---|---|
| 342,131 | 5/1886 | Perkins et al. |
| 3,503,402 | 3/1970 | Schulte. |
| 3,756,243 | 8/1973 | Schulte. |
| 3,768,508 | 10/1973 | Schulte. |
| 3,827,439 | 8/1974 | Schulte et al. |
| 4,360,019 | 11/1982 | Portner et al. |
| 4,364,395 | 12/1982 | Redmond et al. |
| 4,544,371 | 10/1985 | Dormandy, Jr. et al. ......... 604/246 |
| 4,557,721 | 12/1985 | Hooven .................................. 604/9 |
| 4,557,722 | 12/1985 | Harris .................................... 604/9 |
| 4,560,375 | 12/1985 | Schulte et al. ........................ 604/9 |
| 4,588,394 | 5/1986 | Schulte et al. ........................ 604/9 |

FOREIGN PATENT DOCUMENTS 0664424 6/1985 Belgium.

OTHER PUBLICATIONS

Letter dated Dec. 21, 1983 from Dr. Robert R. Smith to Mr. Sarro.
Drawing of the N.Y.U. Volume Control Valve.
A product research document entitled "Implantable Devices for Drug Delivery to the Circulatory and Central Nervous Systems" by Robert H. Pudenz, M.D.

Primary Examiner—C. Fred Rosenbaum
Assistant Examiner—Gene B. Kartchner
Attorney, Agent, or Firm—Kelly, Bauersfeld & Lowry

[57] ABSTRACT

A totally subcutaneously implantable infusion reservoir and pump system includes a variable capacity reservoir for receiving and storing fluid medication for delivery to a catheter which directs the medication to a specific infusion location in the body. In a preferred form of the invention, a control assembly is interposed between the reservoir and the catheter to facilitate and control the transfer of the medication from the reservoir to the catheter in a safe and efficient manner. This control assembly includes a normally closed valve and a pump, both of which are manually actuable by percutaneous pressure when subcutaneously implanted, and defines a portion of a fluid flow conduit between the reservoir and the catheter. Moreover, the control assembly is constructed to prevent the backflow of fluid from the catheter to the reservoir, as well as the unrestricted flow of medication through the control assembly when the normally closed valve is opened. This is accomplished by requiring at least two deliberate and sequential applications of selective pressure to the control assembly before any medication stored in the reservoir can be transferred to the catheter.

20 Claims, 8 Drawing Figures

SUBCUTANEOUS INFUSION RESERVOIR AND PUMP SYSTEM

RELATED APPLICATION

This is a continuation-in-part of U.S. patent application Ser. No. 590,349, filed Mar. 16, 1984 now U.S. Pat. No. 4,588,394.

BACKGROUND OF THE INVENTION

This invention relates generally to infusion systems for the administration of medications and, more particularly, to a refillable and subcutaneously implantable infusion reservoir and pump system useful for pain management in the treatment of terminally ill patients.

It has been found in the treatment of many terminally ill patients that the administration of various medications over sustained periods of time is necessary. For instance, it is often desirable to provide a pain killer, such as morphine, to such patients to help them cope with the sometimes excruciating pain which accompanies certain diseases. Frequently, terminally ill patients experience such extreme pain that hospitalization becomes necessary to provide the patient medications at intervals and in quantities sufficient to meet the patient's needs. Alternatively, when hospitalization is not acceptable, the patient is often required to obtain private nursing care.

Requiring a terminally ill patient to either be hospitalized or to arrange for private nursing care can result in substantial burdens being imposed upon both the health care system and the patient. Health care facilities are increasingly burdened as the demand for hospital bed space increases at a rate greater than the growth in available bed space. This burden is accentuated when patients, such as terminally ill patients, are hospitalized for want of an alternative treatment methodology. Also, the diversion of medically trained personnel to deal with the routine infusion of medications to terminally ill patients imposes additional burdens on the health care system which could be avoided, provided the proper technology were available.

When patients must be confined to a hospital bed or arrange for private duty nursing care to receive prescribed medications, the costs involved often exceed the financial means of such patients. For example, many terminally ill patients cannot afford to pay for the very expensive and individualized care which could make the last period of time prior to death much more productive and less difficult for the patient and for those around him. Indeed, some patients cannot afford any medical care whatsoever and their only available alternative is to foregoin treatment. Sometimes patients who cannot afford the hospitalization or private nursing care required and who cannot tolerate the pain involved with a particular disease must be hospitalized at society's expense.

These burdens to the patient, the health care system and to society in general have prompted several changes in health care methodology. For instance, many physicians have found it desirable to administer prescribed medications on an out-patient basis. This out-patient technique has proven to be effective in substantially reducing the costs associated in the treatment of many types of ailments; however, there have been a number of drawbacks which have made such out-patient arrangements less then ideal.

A typical drawback of out-patient treatment programs includes the requirement of frequent visits by the patient with the physician and the resultant time and transportation problems. It is generally recognized that if the patient could be provided adequate home care for extended periods of time, the time between visits with the physician could be lengthened. Such extended home care would benefit the physician, as well as the patient, in many circumstances by permitting the physician to devote more professional time to other important matters.

Notwithstanding the foregoing, some patients find that receiving regular injections of medications over a prolonged period of time is distasteful, not to mention painful. Additionally, it has been found that repeated injections through the skin into a specific, limited area of the body can be harmful to the patient and can sometimes cause problems which could become more threatening to the well-being of the patient than the illness being treated. Such problems have made necessary the use of alternate injection sites, the rotation of injections among alternate injection sites, or, at the extreme, the abandonment of medication injections as a useful form of treatment.

Moreover, some substances have been found to traumatize the skin when injected, and this has necessitated the use of alternate means for introducing such substances into the body. Such alternate introduction means have included the use of catheters which are inserted through the skin into the body and have a portion which remains extended through the patient's skin to provide external access. This and similar methods and systems have proven to be undesirable for extended treatment because of the risk of infection at the incision site where the catheter extends through the skin.

Accordingly, there has been a need in the medical arts for a system, including the appropriate devices, which allows the patient or his loved ones to administer required medications in precise quantities while minimizing the number of injections required and visits which need be made with a physician. Such a system should be constructed for total subcutaneous emplacement in the body, include appropriate devices to prevent the unintended infusion of the medications from the system into the body, and be refillable, such as by injection, to permit long term use. The present invention fulfills these needs and provides other related advantages.

SUMMARY OF THE INVENTION

The present invention resides in an infusion reservoir and pump system useful, for example, in the administration of medications to patients requiring infusions of medications at relatively frequent intervals and over extended periods of time. More particularly, the system is useful in the administration of pain killers directly into the central nervous system of terminally ill patients. In accordance with the present invention, the system, which is constructed for subcutaneous placement within the patient's body, generally includes a variable capacity reservoir which receives and stores the medications to be administered, a catheter which can be positioned to direct the medications to a selected portion of the patient's body, and a pump and valving arrangement useful for transferring the medications from the reservoir to the catheter and for preventing the unintended passage of the medications from the reservoir into the catheter for delivery to the patient.

In the illustrated embodiment, an injection site apparatus capable of receiving the medications to be infused into the patient by injection is positioned separately within the patient with respect to the reservoir, and is connected thereto by surgical tubing. The injection site apparatus includes a self-sealing dome and a relatively rigid base, which dome and base enclosed an injection chamber. Fluid medication injected into the injection chamber freely flows through the surgical tubing from the injection site apparatus to the reservoir to fill the same. An outlet of the injection site apparatus includes a one-way valve to prevent any reverse flow of fluid from the reservoir to the injection chamber.

The pump and valving arrangement preferably forms a portion of a fluid flow conduit between the reservoir and the catheter, an is shown as a control assembly having a normally closed valve and a pump, both of which are manually actuable by percutaneous pressure when subcutaneously implanted. In a manner similar to that disclosed in my copening U.S. patent application Ser. No. 590,349, now U.S. Pat. No. 4,588,394 the entirety of which is incorporated herein by reference, the normally closed valve is coactive with the pump to require at least two deliberate and sequential applications of selective pressure to the control assembly before the medication stored in the reservoir can be transferred to the catheter. More specifically, the pump and valving arrangement requires a deliberate and sequential, two-step procedure to fill and empty a pumping chamber within the pump. This procedure makes the inadvertent introduction of medication into the patient highly unlikely.

The illustrated control assemblies provide this safeguard with the inclusion of an integral flow occluder which is constructed and positioned with respect to the normally closed valve to inherently prevent the outflow of fluid from the control assembly when the normally closed valve is opened. Only after the selective pressure has been removed from the normally closed valve, can fluid be forced from the pump, again through the selective application of pressure, and out the control assembly for delivery to the catheter. Additionally, the control assembly includes a one-way valve within the assembly outlet to prevent any reverse flow of fluid from the catheter into the pump.

In a preferred form, the normally closed valve utilizes a flexible and resiliently biased valve diaphragm to generally underlie and close a valve passageway within the normally closed valve. This valve diaphragm can be displaced to uncover the valve passageway by applying percutaneous pressure to an overlying cover of the normally closed valve in a manner insuring closure of the integral flow occluder. In another preferred form, the normally closed valve includes a housing constructed or a resiliently flexible material, which encloses a rigid valve stem extending through the valve passageway. This stem is normally biased to prevent flow through the valve passageway unless forceably displaced.

The catheter can be inserted into any portion of the body, such as the lateral ventricle of the brain or the lumbar subarachnoid space. In either of these exemplary configurations, the system provides an efficient and convenient apparatus and method for the administration of medications directly into the central nervous system of terminally ill patients. While such catheter placements are presently contemplated primarily to enhance the treatment of terminally ill patients, it is conceivable that the infusion reservoir and pump system of the present invention could be useful in other medical applications; for instance, in the administration of insulin to diabetic patients.

In addition to the use of standard surgical tubing, the various components of the system of the present invention may be placed in fluid communication with each other through use of flexible, substantially inelastic materials such as Teflon tubing by means of a friction connector assembly. The particular friction connector assembly illustrated herein utilizes an elastic silicone sleeve which is compressed to securely hold an end of the substantially inelastic tubing within the connector assembly.

When the system of the present invention is surgically emplaced subcutaneously within a patient, it is deemed generally preferable to locate the injection site apparatus and the reservoir near softer areas of the body where the skin can be manipulated to allow the injection site apparatus and the reservoir to be percutaneously grasped. Typically, the reservoir will be located in a position remote from the catheter in the abdominal cavity, below the ribs, near a clavicle, or in any other suitable position the surgeon may choose.

Besides forming a single, integral control assembly, the pump and valving arrangement can be constructed from separate, coactive components, each forming independent portions of the fluid flow conduit leading from the reservoir to the catheter. Notwithstanding the configuration of the pump and valving arrangement, it is preferable to locate each component of such generally adjacent a boney surface to provide the desired resistance to movement when the components are percutaneously manipulated. For instance, the pump and valving arrangement could be located adjacent a rib, a clavicle or an iliac crest depending on the insertion point of the catheter and the preferences of the surgeon.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the drawings for purposes of illustration, the present invention is concerned with a subcutaneous infusion reservoir and pump system, generally designated by the reference number 10. This infusion reservoir and pump system 10 generally comprises a variable capacity reservoir 12 connected by a fluid flow conduit 14 to a catheter 16 which directs medications stored in the reservoir to a specific location within the patient. A pump and valving arrangement 18 is also provided to prevent or reduce the likelihood of an inadvertent infusion into the patient of medications stored in the reservoir 12.

The pump and valving arrangement 18 used in the system 10 can be situated between the reservoir 12 and the catheter 16 to form a portion of the fluid flow conduit 14, and the pump and valving arrangement can include one or more normally closed valves. Such a system would require fluid medication to flow through the pump and valving arrangement 18 before passing into the catheter 16, and with the safety and well-being of the patient an all-important consideration in the employment of the system 10, this flow path requirement provides the control over the flow of the medication which is critical to the system's safe use. Indeed, a pump and valving arrangement can be provided which practically eliminates the chance of inadvertently infusing more than a very small quantity of medication into the patient, by requiring specific sequential and deliberate steps to be taken before a measured volume of fluid can be pumped through the system 10.

The subcutaneous infusion reservoir and pump system 10 can substantially reduce the cost of treating some illnesses by eliminating the need for constant medical attention or by reducing the number of required visits which need be made with a physician. The overall design of the system 10 increases its utility for physicians and patients in that the system can be constructed in a variety of configurations for use in many types of different applications. Additionally, the system 10 may be used advantageously by patients requiring regular infusions by minimizing the number of injections received. Moreover, the inherent safety and utility of the infusion reservoir and pump system 10 will permit a patient's family or other loved ones to care for the patient in the privacy of the home and, particularly for terminally ill patients, make the period of illness much more productive and less difficult for the patient and those around him.

In accordance with the present invention, and as illustrated with respect to a preferred embodiment in FIGS. 1-5 and 7, the variable capacity reservoir 12 comprises a silicone elastomer shell 20 which can expand and collapse to accommodate changing volumes of fluid medications. The reservoir 12 includes inlet and outlet apertures 20 and 22 through the reservoir shell 20, which apertures are positioned to permit passage therethrough of flexible tubing, such as surgical tubing. More particularly, a segment of flexible tubing 26 is passed through the inlet aperture 22, and a seal is formed in a conventional manner between the flexible tubing and that portion of the reservoir shell 20 surrounding the inlet aperture. The flexible tubing 26 extends from a point approximately midway through the interior of the reservoir 12, through the inlet aperture 22, and to an independently positionable injection site apparatus 28 which will be described in further detail below. Another segment of flexible tubing 30 likewise extends from approximately the center of the reservoir 12, through the outlet aperture 24, to a control assembly 32 forming the pump and valving arrangement 18 mentioned above, which control assembly will also be further discussed below. The portion of the reservoir shell 20 surrounding the outlet aperture 24 is sealed in a conventional manner to the flexible tubing 30 to prevent the escape of any fluids from the reservoir 12 except through the flexible tubing 30.

Those portions of the flexible tubing 26 and 30 situated within the variable capacity reservoir 12 include a plurality of tube apertures 34. The positioning of the flexible tubing 26 and 30 so that each extends from approximately the center of the reservoir 12, together with the provision of the tube apertures 34, helps insure that a flexible tube fluid passageway will be provided through the center of the reservoir for channeling fluid medications into or out of the reservoir notwithstanding a collapse of the reservoir shell 20. To this end, the flexible tubing is preferably constructed of a resilient silicone elastomer material. For example, the portion of the flexible tubing 30 situated within the reservoir 12 insures that fluid medications will be able to exit the reservoir 12 even when the reservoir shell 20 collapses in a manner which would otherwise occlude the outlet aperture 24.

In systems 10 designed for use in the treatment of terminally ill patients, a reservoir 12 having a thirty milliliter capacity would normally hold sufficient amounts of morphine or other similar pain killing drugs to supply patients sufficient quantities of medications for several days. The variable capacity reservoir 12 can be remotely located from the insertion point of the catheter 16 in any suitable position as the surgeon chooses, such as in the abdominal cavity, below the ribs or near the clavicle. Indeed, the reservoir 12 can be placed in any soft area of the body which would permit the reservoir to be percutaneously grasped while subcutaneously implanted. If necessary to aid in the positioning of the reservoir 12, suture tabs (not shown) could be integrally formed with the reservoir shell 20 to permit the surgeon to anchor the reservoir 12 at the selected location within the patient to prevent migration of the reservoir to an undesirable location.

Figure 7:
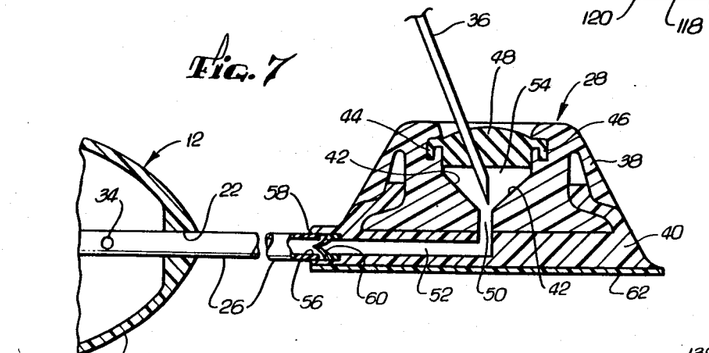
FIG. 7 is an enlarged, fragmented sectional view taken generally along the line 7—7 of FIG. 1, illustrating an injection site apparatus and a portion of a variable capacity reservoir connected to the injection site apparatus by flexible tubing.

The injection site apparatus 28 is shown as being separated from the reservoir 12, and in such a configuration the possibility of puncturing the reservoir during injection with a needle 36, is eliminated. The injection site apparatus 28 includes a rigid polypropylene body 38 forming a needle-shield for the injection site apparatus, and the body is securely mounted to a silicon elastomer base 40. The rigid body 38 provides a funnel-like upper surface 42, which surface further includes indents 44 into which a peripheral rim 46 of an overlying self-sealing dome 48 is positioned to form a fluid-tight seal between the dome and the rigid body. The self-sealing dome 48 is constructed of a silicone elastomer material, such materials providing acceptable levels of tissue reaction when subcutaneously implanted, which can be pierced by a twenty-five gauge or smaller needle 36 without affecting the ability of the dome to re-seal after the needle has been withdrawn.

A channel 50 is provided through the base of the rigid body 38, which channel is aligned with a similar channel 52 through the base 40. These channels 50 and 52 together form a fluid passageway extending from an injection chamber 54 enclosed and defined by the self-sealing dome 48 and the rigid body 38, to the flexible tubing 26. The flexible tubing 26 includes an inlet end 56 sealingly secured within an outlet 58 of the injection site apparatus 28 in a conventional manner to prevent the escape of fluids between the flexible tubing and the base 40. This inlet end 56 of the flexible tubing 26 also includes a one-way valve 60 situated therein to prevent any reverse flow of fluid from the reservoir 12 back to the injection chamber 54. In such a configuration the reverse flow of fluid medication from the reservoir 12 into the injection chamber 54 is prevented even when the fluid pressure within the reservoir is greater than the fluid pressure within the injection chamber. This unidirectional flow feature provides a safety mechanism for the system 10 which prevents the escape of medications stored within the reservoir 12 through the injection site apparatus 28, and minimizes problems which could occur if medications began to leak through the self-sealing dome 48.

The silicone elastomer base 40 of the injection site apparatus 28 is firmly affixed to a reinforced silicone sheet 62. This reinforced sheet 62 helps give the entire injection site apparatus 28 an inherent toughness which can withstand the multiple instances that such injection site apparatus will likely be percutaneously manipulated and pierced with the needle 36. Moreover, this reinforced sheet 62 is affixed to the underside of the base 40 to provide a sturdy peripheral flange for the injection site apparatus 28, which flange in effect provides a continuous suture tab to allow the surgeon to anchor the injection site apparatus at the selected location within the patient to prevent migration of the injection site apparatus to an undesirable location.

Although the injection site apparatus 28 is illustrated in the accompanying drawings as being remotely located from the reservoir 12, it can in fact be located in any suitable position as the surgeon chooses, including locations immediately adjacent the reservoir 12 in the abdominal cavity, below the ribs or near the clavicle. Indeed, the injection site apparatus 28 can be placed in any soft area of the body which would permit the injection site apparatus to be percutaneously grasped while subcutaneously implanted.

It should be apparent that the flexible tubing 30 extending from the reservoir 12 to the control assembly 32 forms a portion of the fluid flow conduit 14 discussed briefly above. Although the flexible tubing 30 extending from the reservoir 12 to the control assembly 32 is shown as passing through the reservoir shell 20, connectors could easily be attached to the reservoir shell for connecting the flexible tubing exteriorly to the reservoir 12 by means of a friction seal.

As the fluid medications are transferred from the reservoir 12 through the fluid flow conduit 14 to the catheter 16, the medications pass through the pump and valving arrangement 18. As illustrated in FIGS. 1 through 5, the pump and valving arrangement 18 comprises the integral control assembly 32 which is attached to the flexible tubing 30 carrying fluid medications that have exited the reservoir 12. The control assembly 32 forms a portion of the fluid flow conduit 14 between the reservoir 12 and the catheter 16, and is situated so that a control assembly inlet 64 is in open fluid communication with the reservoir 12, and a control assembly outlet 66 is in open fluid communication with the catheter inlet.

The control assembly 32 provides a normally closed valve 68, a pump 70, a one-way inlet valve 72, and a one-way outlet valve 74 within the fluid flow conduit 14. These components of the control assembly 32 are so arranged with respect to each other as to require a sequential, two-step application of selective percutaneous pressure when subcutaneously implanted before permitting the passage of medication from the reservoir 12 to the catheter 16. Moreover, because percutaneous pressure must be applied to the assembly 32 to open the normally closed valve 68 when subcutaneously implanted, it is preferable to locate the assembly generally adjacent a bone. Thus, in many instances the control assembly 32 is provided suture tabs which allow the surgeon to anchor the assembly and insure that it remains in the location selected by the physician.

The control assembly 32 is constructed to include a generally planar, rigid floor plate 76, and an overlying stiffly resilient, yet flexible housing 78. Affixed to a portion of the floor plate 76 is a relatively rigid diaphragm support 80, which in turn supports a rigid diaphragm cap 82. The support 80 and the cap 82 are situated and configured between the housing 78 and the floor plate 76 to provide the normally closed valve 68 an inlet chamber 84 in fluid communication with the assembly inlet 64, an outlet chamber 86 which overlies the inlet chamber, and a valve passageway 88 (formed by the diaphragm cap 82) between the inlet and outlet chambers.

A resiliently flexible valve diaphragm 90, constructed to form a dome-shaped member, is seated circumferentially upon the diaphragm support 80 within the inlet chamber 84 so that a portion of the diaphragm is normally positioned adjacent the valve passageway 88. This valve diaphragm 90 is provided a plurality of diaphragm apertures 92. Unless forceably displaced away from the portion of the cap 82 surrounding the valve passageway 88, the diaphragm 90 forms a seal with that adjacent portion of the cap, and prevents any fluid flow through the normally closed valve 68. It is preferred that the cap 82 and the diaphragm 90 be constructed of different materials which will not stick to one another, particularly after lone periods of storage.

Figure 4:
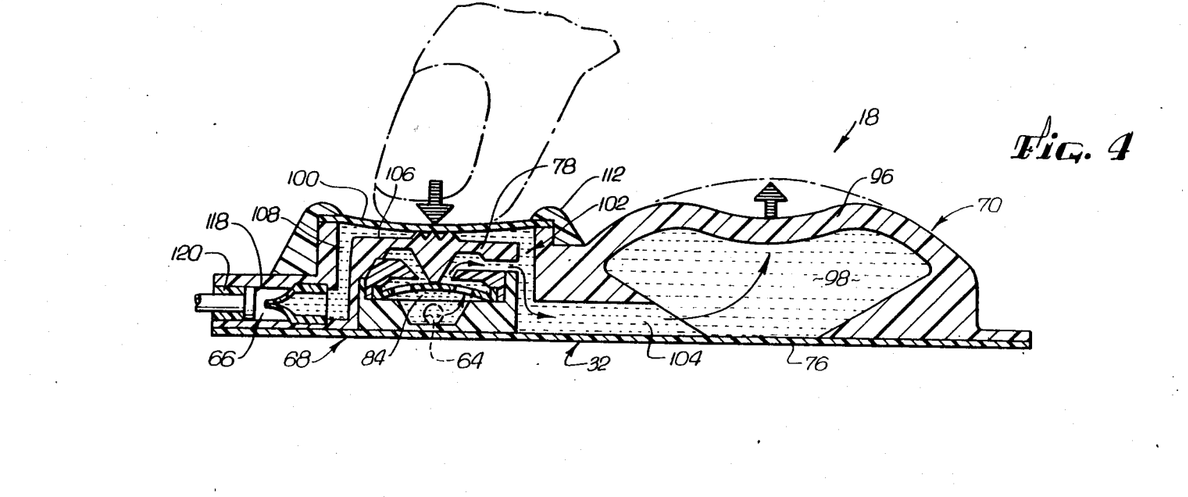
FIG. 4 is an enlarged, fragmented sectional view, similar to FIGS. 2 and 3, of the control assembly, illustrating the manner in which the normally closed valve is opened to permit the filling of the pumping chamber while simultaneously preventing the flow of fluid out of the control assembly through the provision of an integral flow occluder.
Figure 5:
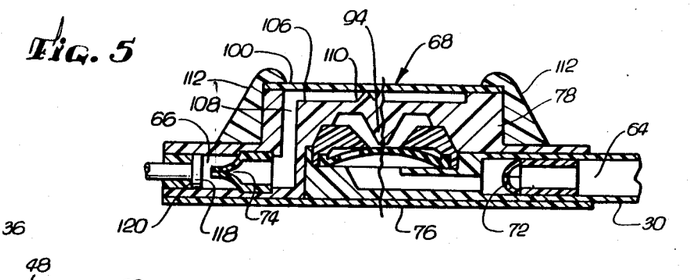
FIG. 5 is an enlarged, fragmented sectional view taken generally along the angulated line 5—5 of FIG. 1, illustrating more clearly the inlet to the normally closed valve.

The portion of the housing 78 overlying the outlet chamber 86 includes a downwardly extending diaphragm displacement finger 94 positioned directly above the valve passageway 88. The finger 94 is situated for travel through the valve passageway 88 when pressed downwardly, and the diameter of the lower portion of the finger is small enough to prevent the occlusion of the valve passageway when the finger is pressed therethrough. When enough pressure is applied, the finger 94 causes the valve diaphragm 90 to flex downwardly a sufficient distance to break the valve seal and allow fluids to pass through the valve passageway 88 (FIG. 4). The housing 78 and the valve diaphragm 90 are each sufficiently resilient to return to their normal configurations and, consequently, close the normally closed valve 68 to fluid flow when the deforming pressure is removed. The inclusion of such a normally closed valve 68 in the system 10 enhances the system's utility and safety by preventing the flow of fluids through the fluid flow conduit 14 in the absence of direct, selectively applied percutaneous pressure on the control assembly 32.

The pump 70, which receives fluids from the normally closed valve outlet chamber 86, comprises a crown 96 formed by the housing 78, which overlies a substantial part of the floor plate 76 to enclose and define a pumping chamber 98. The pumping chamber 98 preferably has an evacuation capacity of one milliliter, and the crown 96, which is resiliently biased to generally maintain a dome or arch-shape, can be deformed to lie substantially flat against the floor plate 76. The volume of the pumping chamber 98 can be customized to accommodate various intended uses for the system 10 and the required dosage to be infused into the patient per pumping stroke. By constructing the housing 78, and therefore the crown 96, of a silicone elastomer material, medication can be injected, if necessary, directly into the pumping chamber 98, the floor plate 76 functioning as a needle guard, and the puncture site will tend to close upon itself and seal the crown when the needle 36 is removed.

A flexible occluder wall 100 is provided over that portion of the housing 78 forming the normally closed valve 68, and defines, in connection with the housing, a fluid exit passageway 102 from the pumping chamber 98 to the one-way valve 74. More specifically, fluid exiting the pumping chamber 98 typically flows through a common fluid passage 104 which also acts as the pump inlet in the transfer of fluids from the valve 68, then between the occluder wall 100 and the upper surface 106 of that portion of the housing 78 overlying the outlet chamber 86, and finally through an exit passage 108. The portion of the housing 78 overlying the outlet chamber 86 and immediately adjacent the occluder wall 100 is formed with several ridges 110 which help to form a seal with the occluder wall when pressed together to depress the finger 94 through the valve passageway 88.

A hard protective valve sheath (sometimes called a support ring) 112 generally surrounds those portions of the housing 78 wherein the one-way outlet valve 74 and the diaphragm 90 of the normally closed valve 68 are situated, to protect the same from unintentional deformation which might result in the inadvertent passage of fluid through the control assembly 32. As illustrated in the accompanying drawings, the only manner provided for opening the normally closed valve 68 is through the selective downward application of pressure on the occluder wall 100, which simultaneously occludes the fluid exit passageway 102 and prevents the exit of fluid from the control assembly 32. Thus, only after the pressure is released from the occluder wall 100 and the valve 68 is closed, can medication within the pumping chamber 98 be forced out of the control assembly 32 through the fluid exit passageway 102.

The one-way outlet valve 74 is situated near the assembly outlet 66 to prevent the inflow of fluid to the control assembly 32 through the assembly outlet. A control assembly outlet connector 114 extends outwardly from the housing 78 to define the assembly outlet 66. This control assembly outlet connector 114 is designed to engage an inlet end of surgical tubing forming a portion of the fluid flow conduit 14, or, as illustrated, a catheter inlet 116. The end of the outlet connector 114 situated within the housing 78 includes a flange portion 118 which sealingly engages a suture sleeve 120 to form a seal preventing medication from exiting the control assembly 32 other than through the outlet connector.

While the pump and valving arrangement 18 is shown in the exemplary drawings as combined to form the single control assembly 32, the normally closed valve 68 and the pump 70 may be separately constructed to form individual system components which can be connected to one another by a conduit such as the flexible tubing 30.

Figures 1, 2:
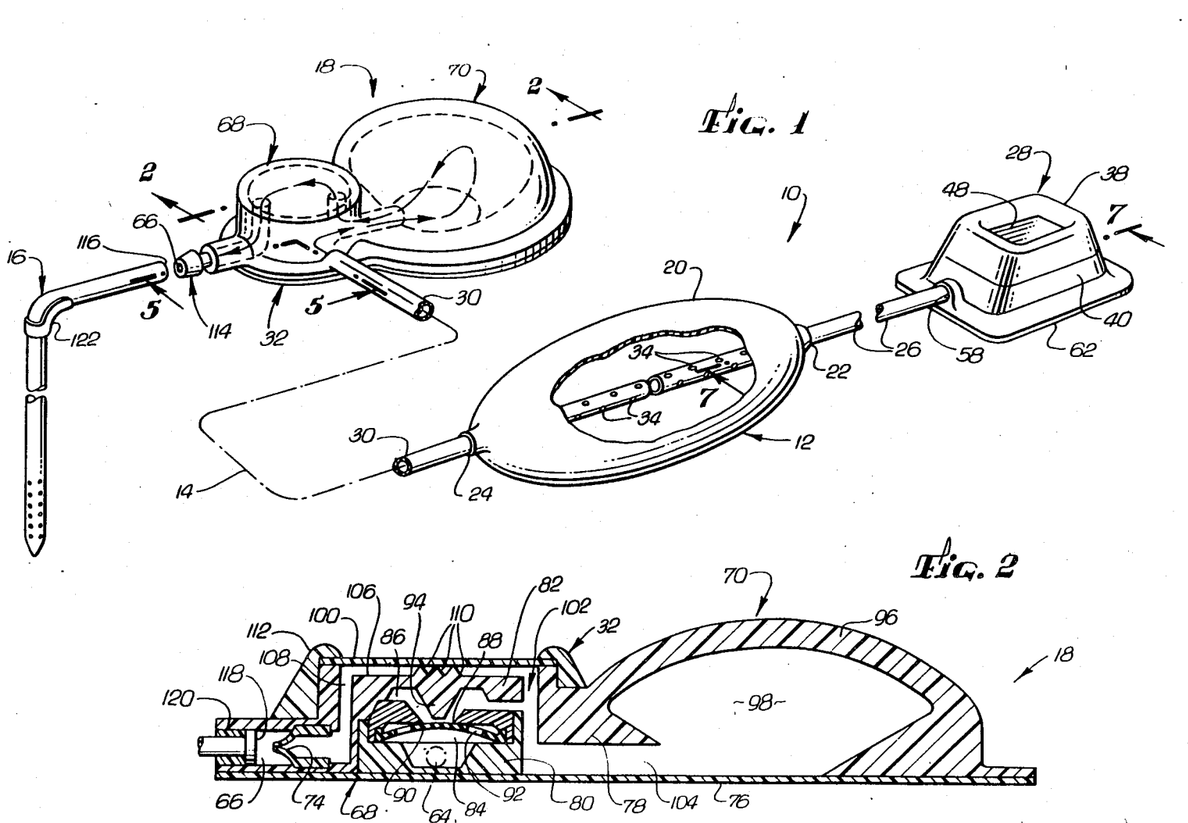
FIG. 1 is a diagrammatic view of a preferred form of the present invention, illustrating the relationship of the various components to each other, and showing a portion of the reservoir shell broken away and the fluid flow path through the pump and valving arrangement in phantom for clarity.
FIG. 2 is an enlarged, fragmented sectional view taken generally along the line 2—2 of FIG. 1, illustrating the configuration of a control assembly forming the pump and valving arrangement when ready for pumping medication to the patient.

The catheter 16 is preferably formed of a barium-impregnated silicone elastomer material which is radiopaque for detection by X-ray photography. The catheter inlet 116 is attached to the control assembly outlet connector 114 by sliding frictional engagement, and fluid medication exiting the control assembly 32 is directed by the catheter 16 for infusion into a specific portion of the body. For example, in the case of terminally ill patients the catheter 16 can be inserted into the lateral ventricle of the patient's brain. When such catheter placement is contemplated, a catheter clip 122, as shown in FIG. 1, can be advantageously utilized to hold the catheter 16 in place adjacent a burr hole through the skull.

Figure 3:
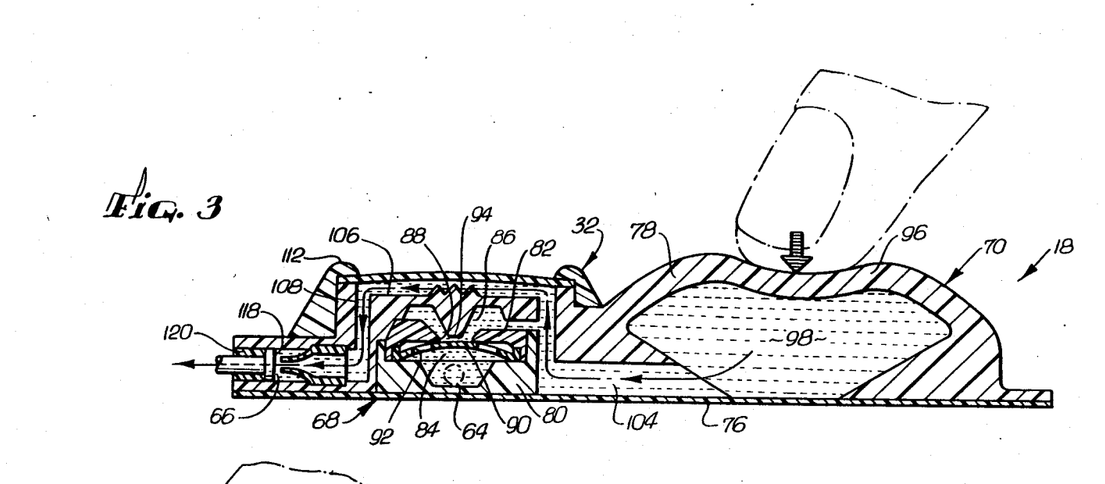
FIG. 3 is an enlarged, fragmented sectional view, similar to FIG. 2, of the control assembly, illustrating the manner in which fluid is pumped from a pumping chamber to the catheter.

The pump and valving arrangement 18 requires a two-step procedure to pump fluid medication from the reservoir 12 to the catheter 16. Before pumping may begin, however, the flexible tubing 26 and 30 between the injection site apparatus 28 and the reservoir 12, and the reservoir and the control assembly 32, must be primed with medication, and the saline solution normally contained within the control assembly during insertion into the patient must be evacuated therefrom. Typically, this preparatory step can be accomplished by simply depressing the pump crown 96 through the selective application of percutaneous pressure as illustrated in FIG. 3. This causes any fluid within the pumping chamber 98 to exit the control assembly 32 through the fluid exit passageway 102 as shown by the arrows. The membrane lips of the one-way outlet valve 74 spread sufficiently to allow such fluid to escape the control assembly 32, but immediately close and prevent the reverse flow of fluid through the fluid exit passageway 102 upon removal of the percutaneous pressure depressing the pump crown 96. The valve diaphragm 96 and the one-way inlet valve 72 prevent fluid within the pumping chamber 98 from passing back into the reservoir 12. After the pumping chamber 98 has been evacuated, the normally closed valve 68 and the one-way outlet valve 74 function collectively to prevent the refilling of the pumping chamber with fluid from the catheter, and the diaphragm 90 prevents fluid from flowing from the reservoir 12. Accordingly, the crown 96 remains in a depressed or collapsed position until the normally closed valve 68 is opened.

After this preparatory step has been completed, the pump 70 and valve 68 can be repeatedly percutaneously manipulated to transfer measured quantities of medication from the reservoir 12 to the catheter 16 for infusion into a patient. To begin, the first step includes the selective application of pressure to the occluder wall 100 to depress the finger 94 downwardly through the valve passageway 88 sufficiently to break the seal between the flexible valve diaphragm 90 and the adjacent portion of the cap 82. This permits fluid medication to flow from the inlet chamber 84 through the valve passageway 88 into the outlet chamber 86, then through the common passage 104 and into the pumping chamber 98. The biasing and resiliency of the pump crown 96 tends to draw the fluid medication through the normally closed valve 68 to fill the pumping chamber 98 until the crown 96 has resumed its dome or arch-shape (FIG. 4). At times where the biasing and resiliency of the pump crown 96 is not sufficient to cause fluid flow through the system 10, the reservoir 12 can be percutaneously palpated to create adequate fluid pressure through the fluid flow conduit 14 to completely fill the pumping chamber 98.

The construction of the control assembly 32 to include the occluder wall 100 capable of preventing the flow of fluid through the fluid exit passageway 108, adds an important safety feature to the infusion reservoir and pump system 10. As illustrated and described, there can never be more than the volume of fluid contained within the pumping chamber 98 which can pass through the control assembly 32 into the catheter 16 each time the valve 68 is opened. Whenever the valve 68 is opened, the occluder wall 100 interacts with the ridges 110 to block flow of medication through the fluid exit passage 108, and thus prevent any medication from passing through the control assembly 32 while the pumping chamber 98 is being refilled. In essence, the control assembly 32 provides a simplified pump and valving arrangement 18 within the fluid flow conduit 14 which never allows the reservoir 12 to be placed in opened communication with the catheter 16, and risk an excessive transfer of medication through the system 10 to the patient.

After the pumping chamber 98 is filled with medication, the selective pressure can be withdrawn from the occluder wall 100, allowing the resiliently biased valve diaphragm 90 to again become positioned to block fluid flow through the valve passageway 88. To transfer the medication from the pumping chamber 98 through the control assembly 32 to the catheter 16, the second step simply requires the selective application of pressure to depress the pump crown 96, to evacuate medication from the pumping chamber 98 through the fluid exit passageway 102 and out the assembly outlet 66. As described previously, the seal between the valve diaphragm 90 and the surrounding portion of the cap 82 will prevent the passage of fluid in either direction through the valve passageway 88 unless forcefully depressed by the displacement finger 94, and the one-way outlet valve 74 permits only the outflow of medication or other fluids from the control assembly 32 as the crown 96 is depressed. Once the pump crown 96 has been depressed toward the underlying part of the floor plate 76, the pressure applied can be released, leaving the pump crown 96 in the deflected or depressed position, and the control assembly 32 is once again ready for another pumping cycle which would begin with the opening of the normally closed valve 68 through another selective application of percutaneous pressure.

It is evident from the foregoing that the sequential two-step pumping procedure described prevents the inadvertent infusion of medications through the system 10 which could result in harm to the patient. All of these foregoing features evident from the description of the above-described subcutaneous infusion reservoir and pump system 10, can be found in a modification of the control assembly 32 to include an alternate-type of normally closed valve 124.

Figure 6:
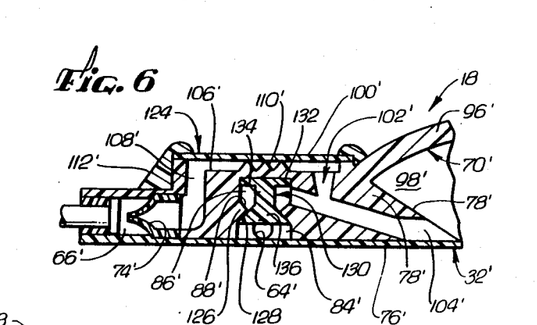
FIG. 6 is an enlarged sectional view of an alternate form of the normally closed valve, this particular view illustrating the manner in which the alternate normally closed valve would be attached to a pump to form an alternate control assembly if sectioned along the line 2—2 of FIG. 1.

As illustrated in FIG. 6, the modified control assembly 32' is constructed and operates in a manner very similar to that of the above-described control assembly 32. More specifically, the modified control assembly 32' is constructed to include a generally planar, rigid floor plate 76', and an overlying stiffly resilient, yet flexible housing 78'. The housing 78' is configured to provide the alternate normally closed valve 124 an inlet chamber 84' in fluid communication with an assembly inlet 64', an outlet chamber 86' which overlies the inlet chamber, and a valve passageway 88' between the inlet and outlet chambers.

As was the case with the embodiment illustrated in FIG. 1, the flexible housing 78' can be constructed of a silicone elastomer material in a manner permitting the housing to re-seal if punctured by a needle. The modified assembly inlet 64' is configured to internally receive an end of the flexible tubing 30, which in turn is fused within the inlet to place the modified control assembly 32' in open fluid communication with the reservoir 12. Fluid flowing through the assembly inlet 64' initially enters the inlet chamber 84' formed between the flexible housing 78' and the floor plate 76'. Fluid within the inlet chamber 84' must await the opening of the alternate normally closed valve 124 before flowing into the pump 70'.

The outlet chamber 86', which is in open fluid communication with the pump 70', is provided within the normally closed valve 124. A portion of the outlet chamber 86' is situated to generally overlie the inlet chamber 84' so that the valve passageway 88' through an intermediate portion 126 of the housing 78' can provide a fluid flow path between the inlet chamber 84' and the outlet chamber 86'. The intermediate portion 126 of the housing 78' generally surrounding this valve passageway 88' has a lower tapered surface which forms a valve seat 128.

A generally T-shaped valve stem 130 is provided within the valve passageway 88' extending from the outlet chamber 86' through the valve passageway 88' and into the inlet chamber 84'. The valve stem 130 includes an upper expanded section 132 which is securely attached to an upper ceiling of the outlet chamber 86' in a manner causing the valve stem 130 to move in response to any movement of the upper ceiling surface. The valve stem 130 also includes a shaft 134 which extends downwardly from the upper expanded section 13 through the valve passageway 88' and into the inlet chamber 84' where this shaft enlarges slightly to form a lowered tapered foot 136 having a shape which cooperates with the taper of the valve seat 128. In the normally closed position, this lower foot 136 contacts the valve seat 128 to seal the valve passageway 88' and prevent fluid flow between the inlet chamber 84' and the outlet chamber 86'. The outlet chamber 86' is also sufficiently large to accomodate movement of the upper expanded section 132 of the valve stem 130 and still permit fluid flow therethrough. The valve stem 130 is constructed of a material different from the material of the housing 78' to reduce valve seat to valve stem sticking. For instance, the valve stem 130 can be constructed of a polypropylene material to reduce the possibility of sticking to a silicone elastomer valve seat 128 during storage, handling, shipping or use of the valve 124.

With the exception of the foregoing noted differences between the modified control assembly 32' illustrated in FIG. 6, and the control assembly 32 illustrated in FIG. 1, the construction and operation of the respective control assemblies are identical. To illustrate the point, the pump 70', which receives fluid from the alternate normally closed valve outlet chamber 86', comprises a crown 96' formed by the housing 78', which overlies a substantial part of the floor plate 76' to enclose and define a pumping chamber 98'. The pumping chamber 98' also preferably has an evacuation capacity of one milliliter, and the crown 96', which is resiliently biased to generally maintain a dome or arch-shape, can be deformed to lie substantially flat against the floor plate 76'.

A flexible occluder wall 100' is provided over that portion of the housing 78' forming the alternate normally closed valve 124, and defines, in connection with the housing and a hard, protective valve sheath 112', a fluid exit passageway 102' from the pumping chamber 98' to the one-way outlet valve 74'. More specifically, fluid exiting the pumping chamber 98' typically flows through a common fluid passage 104' which also acts as the pump inlet in the transfer of fluids from the valve 68', then between the occluder wall 100' and the upper surface 106' of that portion of the housing 78' overlying the outlet chamber 86', and finally through an exit passage 108'. That portion of the housing 78' overlying the outlet chamber 86' and immediately adjacent the occluder wall 100' is formed with several ridges 110' which help to form a seal with the occluder wall when pressed together to move the valve stem 130 through the valve passageway 88', and separate the lower tapered foot 136 from the valve seat 128 to open the valve 124.

The sheath (sometimes called a support ring) 112', generally surrounds those portions of the housing 78' wherein the one-way outlet valve 74' and the valve stem 130 of the normally closed valve 124 are situated, to protect the same from unintentional deformation which might result in the inadvertent passage of fluid through the alternate control assembly 32'. The only manner provided for opening the alternate normally closed valve 124 is through the selective downward application of pressure on the occluder wall 100', which simultaneously occludes the fluid exit passageway 102' and prevents the exit of fluid from the modified control assembly 32'. Thus, only after the pressure is released from the occluder wall 100' and the valve 124 is closed, can medication within the pumping chamber 98' be forced out of the control assembly 32' through the fluid exit passageways 102' and 108'.

Figure 8:
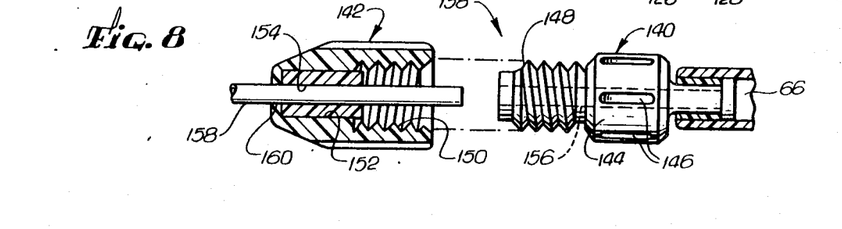
FIG. 8 is an enlarged, fragmented and partially sectional view of a friction connector which can be used with the system of the present invention to connect flexible, substantially inelastic tubing between the other components to place the same in fluid communication with one another.

Although the various individual components of the subcutaneous infusion reservoir and pump system 10 illustrated in the accompanying drawings will typically be connected to one another by surgical tubing either fused within inlet and exit openings, or frictionally connected to one or more connector assemblies, the present invention further contemplates use of flexible, substantially inelastic tubing, such as tubing constructed of the material known as Teflon. To this end, and as illustrated in FIG. 8, a different type of connection between the inelastic tubing to the various components is preferably utilized, since it may be undesirable to glue or otherwise fuse the inelastic tubing to the adjacent component, and such alternate flexible tubing further lacks the elasticity necessary to slide over standard connector assemblies to form a frictional fit therewith.

The connector assembly 138 includes generally a connector body 140 and a corresponding connector nut 142. The connector body 140 includes one end positioned and securely held within an inlet or exit opening of any of the system 10 components in a standard fashion, an enlarged portion 144 provided indents 146 intended to provide a secure gripping surface to facilitate handling of the same by the surgeon, and a threaded end portion 148 extending outwardly away from the enlarged portion opposite the component of the system 10 to which the connector body 140 is attached. The connector nut 142 includes an internally threaded portion 150 dimensioned to correspond with the threaded end portion 148 of the connector body 140. A generally cylindrical chamber 152 is provided within the connector nut 142 inwardly of the internally threaded portion 150, wherein a resiliently flexible and elastic sleeve 154 is positioned.

When assembled, the connector body 140, the connector nut 142 and the sleeve 154 provide, in combination, a connector assembly fluid passageway 156 capable of channeling fluids from the adjacent system component to a segment of inelastic tubing. Such tubing, illustrated in FIG. 8 by the reference number 158, is inserted into the connector assembly 138 through an aperture 160 through the distal end of the connector nut 142, and may extend the entire length of the connector assembly passageway 156.

The tubing 158 is held within the connector assembly 138 by a gripping action exerted on the tubing by the sleeve 154 as it is compressed between the cylindrical chamber 152 of the connector nut 142, and the threaded end portion 148 of the connector body 140. In particular, the sleeve 154 is dimensioned to extend a short distance into the internally threaded portion 150 so that as the connector nut 142 is threaded onto the connector body 140, the engaging end of the threaded portion 148 presses the sleeve 154 back into the cylindrical chamber 152. This action causes the elastic sleeve to slightly expand against the outer wall of the adjacent tubing 158 a sufficient amount to form a seal between the sleeve and the tubing, and further securely hold the tubing in place. The provision of such a connector assembly 138 gives the surgeon greater flexibility in determining precisely how the various components of the system 10 will be implanted within the patient, and further the manner in which the various components will be fluidly connected to one another.

The infusion reservoir and pump system 10 described above can greatly ease the burden of medical personnel and hospital facilities by providing means for internally storing a large quantity of medication which is to be administered to a patient over an extended period of time. Moreover, various apparatuses can be added to the system 10 for a multitude of purposes, such as the provision of a burr hole reservoir situated adjacent the skull to facilitate injection of medications directly into the brain.

Although a particular embodiment of the invention and alternate components forming portions thereof have been described in detail for purposes of illustration, various modifications of the system as a whole and the components individually may be made without departing from the spirit and scope of the invention. Accordingly, the invention is not to be limited, except as by the appended claims.

We claim:

1. A subcutaneous infusion reservoir and pump system, comprising:

means for receiving medication into said system by injection;

a reservoir for storing medication injected into said receiving means, said reservoir including a reservoir inlet in fluid communication with said receiving means, and a reservoir outlet;

a normally closed valve capable of being opened to fluid flow therethrough by percutaneous manual manipulation and having a valve inlet in fluid communication with said reservoir outlet, a valve outlet, a resiliently flexible housing, a rigid floor plate underlying said housing to form an inlet chamber therebetween in fluid communication with said valve inlet, an outlet chamber within said housing, said outlet chamber overlying said inlet chamber, a valve passageway situated directly between said inlet and outlet chambers, said valve passageway permitting fluid flow between said inlet and outlet chambers, a valve diaphragm situated within said inlet chamber and resiliently biased to cover said valve passageway, said valve diaphragm normally forming a seal with a portion of said valve surrounding said valve passageway to prevent the flow of fluid through said normally closed valve unless forceably displaced, and a diaphragm displacement finger extending downwardly from the ceiling of said outlet chamber, said diaphragm displacement finger being situated and configured to displace said valve diaphragm and open said normally closed valve to fluid flow therethrough when moved downwardly through said valve passageway;

a pump having a pump inlet in fluid communication with said valve outlet, a pump outlet and a resilient crown defining at least a portion of said pumping chamber, said pump being manually actuable by the selective application of percutaneous pressure to depress said crown;

means for occluding said pump outlet when said normally closed valve is opened to fluid flow therethrough, said means for occluding including an occluder wall overlying the top portion of said housing of said normally closed valve, said occluder wall defining, in connection with the adjacent portion of said housing, a fluid exit passageway in communication with said pump outlet, said occluder wall preventing the flow of fluid through said fluid exit passageway when pressed against the adjacent portion of said housing; and a catheter for directing medication to a specific location within the body, said catheter having a catheter inlet in fluid communication with said pump outlet.

2. A system as recited in claim 1 wherein said housing forms said resilient crown for said pump, and said resilient crown overlies an extension of said floor plate to define said pumping chamber therebetween.

3. A system as recited in claim 1 wherein said receiving means comprises an injection site apparatus providing a self-sealing dome overlying a rigid needle-shield to define an injection chamber therebetween, said needle-shield having an outlet passageway in open fluid communication with an outlet of said injection site apparatus so that said reservoir can be placed in fluid communication with said injection chamber.

4. A system as recited in claim 3 wherein said reservoir includes a flexible outer body capable of expanding to accommodate varying amounts of medication.

5. A system as recited in claim 4 further including a flexible tube extending from said reservoir outlet into said reservoir to channel fluids through said reservoir outlet notwithstanding a collapse of said reservoir about said reservoir outlet.

6. A system as recited in claim 1 wherein said catheter is constructed of a radiopaque, barium-impregnated silicone elastomer material.

7. A system as recited in claim 1 including means for preventing the flow of fluid through said fluid exit passageway to fill said pumping chamber.

8. A subcutaneous infusion reservoir and pump system, comprising:

means for receiving medication into said system by injection;

a reservoir for storing medication injected into said receiving means, said reservoir including a reservoir inlet in fluid communication with said receiving means, and a reservoir outlet;

a normally closed valve capable of being opened to fluid flow therethrough by percutaneous manual manipulation and including a resiliently flexible housing having an inlet in fluid communication with said reservoir outlet, an outlet, an inlet chamber within said housing, said inlet chamber being in fluid communication with said inlet, an outlet chamber within said housing, said outlet chamber being in fluid communication with said outlet and said outlet chamber generally overlying said inlet chamber, a valve passageway through said housing between said inlet chamber and said outlet chamber, an intermediate portion of said housing generally surrounding said valve passageway and being tapered to form a valve seat, and a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway;

a pump having a pump inlet in fluid communication with said valve outlet, a pump outlet and a resilient crown defining at least a portion of a pumping chamber, said pump being manually actuable by the selective application of percutaneous pressure to depress said crown;

means for occluding said pump outlet when said normally closed valve is opened to fluid flow therethrough, said means for occluding including an occluder wall overlying the top portion of said housing of said normally closed valve, said occluder wall defining, in connection with the adjacent portion of said housing, a fluid exit passageway in communication with said pump outlet, said occluder wall preventing the flow of fluid through said fluid exit passageway when pressed against the adjacent portion of said housing; and a catheter for directing medication to a specific location within the body, said catheter having a catheter inlet in fluid communication with said pump outlet.

9. A system as recited in claim 8, including means for connecting any separately positioned components of said system with flexible, substantially inelastic tubing.

10. A subcutaneous infusion reservoir and pump system, comprising:

means for receiving medication into said system by injection;

a reservoir for storing medication injected into said receiving means, said reservoir including a reservoir inlet in fluid communication with said receiving means, and a reservoir outlet;

a normally closed valve having a valve inlet in fluid communication with said reservoir outlet, and a valve outlet;

a pump having a pump inlet in fluid communication with said valve outlet, a pump outlet and a resilient crown defining at least a portion of a pumping chamber, said pump being manually actuable by the selective application of percutaneous pressure to depress said crown;

means for occluding said pump outlet when said normally closed valve is opened to fluid flow therethrough, said occluding means defining a portion of said pump outlet;

a catheter for directing medication to a specific location within the body, said catheter having a catheter inlet in fluid communication with said pump outlet; and means for connecting any separately positioned components of said system with flexible, substantially inelastic tubing, said connecting means including a connector assembly sealingly anchored at one end to a component of said system, said connector assembly including a connecting body and a corresponding connector nut which can be threaded onto said connector body, said connector nut having an elastic sleeve positioned internally therein through which an end of the flexible, substantially inelastic tubing is placed, which sleeve is compressible by the interaction between said connector body and said connector nut to form a friction seal with the tubing and securely hold the same within said connector assembly.

11. A subcutaneously implantable control assembly comprising:

a resiliently flexible housing;

a normally closed valve formed at least partially by said housing and having a valve inlet and a valve outlet, said normally closed valve being opened to fluid flow therethrough by percutaneous manual manipulation when subcutaneously implanted;

an inlet chamber within said housing, said inlet chamber being in fluid communication with said valve inlet;

an outlet chamber within said housing, said outlet chamber generally overlying said inlet chamber;

a valve passageway situated directly between said inlet and outlet chambers, said valve passageway permitting fluid flow between said inlet and outlet chambers;

a valve diaphragm situated within said inlet chamber and resiliently biased to cover said valve passageway, said valve diaphragm normally forming a seal with a portion of said normally closed valve surrounding said valve passageway to prevent the flow of fluid through said normally closed valve unless forceably displaced;

a diaphragm displacement finger extending downwardly from the ceiling of said outlet chamber, said diaphragm displacement finger being situated and configured to displace said valve diaphragm and open said normally closed valve to fluid flow therethrough when moved downwardly through said valve passageway;

a pump having a pump inlet in fluid communication with said valve outlet, a pump outlet in fluid communication with an assembly outlet, and a resilient crown formed by said housing and defining at least a portion of a pumping chamber, said pump overlying a rigid floor plate to define said pumping chamber therebetween and being manually actuable by the selective application of percutaneous pressure to depress said crown; and means for occluding said pump outlet when said normally closed valve is opened to fluid flow therethrough, said occluding means including an occluder wall overlying the portion of said housing forming said normally closed valve, said occluder wall defining, in connection with the adjacent portion of said housing, a fluid exit passageway between said pump outlet and said assembly outlet, said occluder wall preventing the flow of fluid through said fluid exit passageway when pressed against the adjacent portion of said housing.

12. A control assembly as recited in claim 11 wherein said rigid floor plate underlies said normally closed valve, and said assembly includes a rigid sheath which, in connection with said rigid floor plate, surrounds and forms an exterior portion of said normally closed valve.

13. A control assembly as recited in claim 12 wherein an outlet connector suitable for frictional attachment to surgical tubing forms said assembly outlet.

14. A control assembly as recited in claim 11 including means for preventing the inflow of fluid into said assembly through said assembly outlet.

15. A control assembly as recited in claim 14 wherein said preventing means includes a one-way valve.

16. A subcutaneously implantable control assembly comprising:

a resiliently flexible housing;

a normally closed valve formed at least in part by said housing and having a valve inlet and a valve outlet, said normally closed valve being opened to fluid flow therethrough by percutaneous manual manipulation when subcutaneously implanted;

an inlet chamber within said housing, said inlet chamber being in fluid communication with said valve inlet;

an outlet chamber within said housing, said outlet chamber being in fluid communication with said valve outlet and said outlet chamber generally overlying said inlet chamber;

a valve passageway through said housing between said inlet chamber and said outlet chamber, an intermediate portion of said housing generally surrounding said valve passageway and being tapered to form a valve seat;

a valve stem attached to and extending downwardly from an upper ceiling of said outlet chamber through said valve passageway and into said inlet chamber, said valve stem including a lower foot which cooperates with said valve seat to form a valve seal, said valve seal being replaceably broken when an upper cover portion of said housing overlying said outlet chamber is resiliently deformed to cause the downward movement of said valve stem through said valve passageway;

a pump having a pump inlet in fluid communication with said valve outlet, a pump outlet in fluid communication with an assembly outlet, and a resilient crown formed by said housing and defining at least a portion of a pumping chamber, said pump overlying a rigid floor plate to define said pumping chamber therebetween and being manually actuable by the selective application of percutaneous pressure to depress said crown; and means for occluding said pump outlet when said normally closed valve is opened to fluid flow therethrough, said occluding means including an occluder wall overlying the portion of said housing forming said normally closed valve, said occluder wall defining, in connection with the adjacent portion of said housing, a fluid exit passageway between said pump outlet and said assembly outlet, said occluder wall preventing the flow of fluid through said fluid exit passageway when pressed against the adjacent portion of said housing.

17. A control assembly as recited in claim 16 wherein said rigid floor plate underlies said normally closed valve, and said assembly includes a rigid sheath which, in connection with said rigid floor plate, surrounds and forms the exterior of said normally closed valve with the exception of the surface provided by said occluder wall.

18. A control assembly as recited in claim 17 wherein an outlet connector suitable for frictional attachment to surgical tubing forms said assembly outlet.

19. A control assembly as recited in claim 16, including means for connecting an assembly inlet with a flexible, substantially inelastic tubing.

20. A subcutaneously implantable control assembly comprising:

a normally closed valve having a valve inlet and a valve outlet, said normally closed valve being opened to fluid flow therethrough by percutaneous manual manipulation when subcutaneously implanted;

a pump having a pump inlet in fluid communication with said valve outlet, a pump outlet in fluid communication with an assembly outlet, and a resilient crown defining at least a portion of a pumping chamber, said pump being manually actuable by the selective application of percutaneous pressure to depress said crown;

means for occluding said pump outlet when said normally closed valve is opened to fluid flow therethrough, said occluding means defining a portion of the fluid passageway between said pump outlet and said assembly outlet; and means for connecting said assembly outlet with a flexible, substantially inelastic tubing, said connecting means including a connector assembly sealingly anchored at one end within said assembly outlet, said connector assembly including a connector body and a corresponding connector nut which can be threaded onto said connector body, said connector nut having an elastic sleeve positioned internally therein through which an end of the flexible, substantially inelastic tubing is placed, which sleeve is compressible by the interaction between said connector body and said connector nut to form a friction seal with the tubing and securely hold the same within said connector assembly.

* * * * *

UNITED STATES PATENT AND TRADEMARK OFFICE
CERTIFICATE OF CORRECTION

PATENT NO. : 4,681,560

DATED : July 21, 1987

INVENTOR(S) : Rudolf R. Schulte, et al.

It is certified that error appears in the above-identified patent and that said Letters Patent is hereby corrected as shown below:

In Column 3, line 20, delete the word "copening" and insert therefor --copending--.

In Column 8, line 64, delete the word "lone" and insert therefor --long--.

In Column 12, line 60, delete the "13" and insert therefor --132--.

Signed and Sealed this

Twenty-ninth Day of December, 1987

Attest:

DONALD J. QUIGG

Attesting Officer

Commissioner of Patents and Trademarks